United States Patent
Shi et al.

(10) Patent No.: US 6,664,389 B1
(45) Date of Patent: Dec. 16, 2003

(54) HIGHLY RESISTANT GRANULAR STARCH

(75) Inventors: Yong-Cheng Shi, Neshanic Station, NJ (US); Roger Jeffcoat, Bridgewater, NJ (US)

(73) Assignee: National Starch and Chemical Investment Holding Coporation, New Castle, DE (US)

( * ) Notice: Subject to any disclaimer, the term of this patent is extended or adjusted under 35 U.S.C. 154(b) by 193 days.

(21) Appl. No.: 09/671,523

(22) Filed: Sep. 27, 2000

Related U.S. Application Data

(60) Provisional application No. 60/157,370, filed on Oct. 1, 1999.

(51) Int. Cl.$^7$ .......................... C08B 31/00; C08B 33/00; C08B 30/00; A23L 1/0522
(52) U.S. Cl. ....................... 536/102; 127/65; 127/69; 127/71; 127/32; 426/661
(58) Field of Search ........................... 536/102; 127/65, 127/69, 71, 32; 426/661

(56) References Cited

U.S. PATENT DOCUMENTS 5,051,271 A  9/1991  Iyengar et al. ............... 426/658

(List continued on next page.)

FOREIGN PATENT DOCUMENTS

| EP | 0 846 704 A3 | 6/1998 | ........... C08B/30/12 |
| EP | 0 846 704 A2 | 6/1998 | ........... C08B/30/12 |
| WO | WO 90/15147 | 12/1990 | ........... C12P/19/14 |
| WO | WO 00/55209 | 9/2000 | ........... C08B/30/12 |

OTHER PUBLICATIONS

Pomeranz, Y., "Research and development regarding enzyme–resistant starch (RS)* in the USA: a review", European Journal of Clinical Nutrition (1992) 46 (Suppl. 2): S63–S68 (1992).

Szczodrak, J. and Pomeranz, Y., "Starch and Enzyme–Resistant Starch from High–Amylose Barley", Cereal Chem. 68(6): 589–596 (1991).

Czuchajowska, Z., Sievert, D., and Pomeranz, Y., "Enzyme–Resistant Starch. IV. Effects of Complexing Lipids", Cereal Chem. 68(5): 537–542 (1991).

Sievert, D., Czuchajowska, Z., and Pomeranz, Y., "Enzyme–Resistant Starch. III. X–Ray Diffraction of Autoclaved Amylomaize VII Starch and Enzyme–Resistant Starch Residues", Cereal Chem. 68(1): 86–91 (1991).

Sievert, D. and Pomeranz, Y., "Enzyme–Resistant Starch. II. Differential Scanning Calorimetry Studies on Heat–Treated Starches and Enzyme–Resistant Starch Residues", Cereal Chem. 67(3): 217–221 (1990).

Sievert, D. and Pomeranz, Y., "Enzyme–Resistant Starch. I. Characterization and Evaluation by Enzymatic, Thermoanalytical, and Microscopic Methods", Cereal Chem. 66(4): 342–347 (1989).

Englyst, H.N., Kingman, S.M., and Cummings, J.H., "Classification and measurement of nutritionally important starch fractions", European Journal of Clinical Nutrition (1992) 46 (Suppl. 2): S33–S50.

Englyst, Hans N. and Macfarlane, George T., "Breakdown of Resistant and Readily Digestible Starch by Human Gut Bacteria", J. Sci. Food Agric. (1986) 37: 699–706.

*Primary Examiner*—James Wilson
*Assistant Examiner*—Everett White
(74) *Attorney, Agent, or Firm*—Karen G. Kaiser

(57) ABSTRACT

Highly resistant granular starches may be produced which have unique and useful properties, including high enzyme resistance, dietary fiber, a unique molecular weight distribution, a high melting temperature and a high heat of gelatinization (Delta H) indicative of excellent processing tolerance. These starches may be prepared for example by heating a high amylose starch having at least 40% by weight amylose content and at a percent moisture and temperature insufficient to destroy the granular nature of the starch, and digesting the amorphous regions using alpha-amylase or a chemical reagent.

22 Claims, 1 Drawing Sheet

U.S. PATENT DOCUMENTS

| | | | |
|---|---|---|---|
| 5,300,145 A | 4/1994 | Fergason et al. | 106/213 |
| 5,409,542 A | 4/1995 | Henley et al. | 127/65 |
| 5,593,503 A | 1/1997 | Shi et al. | 127/71 |
| 5,849,090 A | 12/1998 | Haralampu et al. | 127/65 |
| 5,902,410 A | 5/1999 | Chiu et al. | 127/71 |
| 6,013,299 A * | 1/2000 | Haynes et al. | 426/549 |

* cited by examiner

HIGHLY RESISTANT GRANULAR STARCH

This application claims priority from the provisional patent 60/157,370 filed Oct. 1,1999.

FIELD OF THE INVENTION

The present invention relates to a highly resistant, granular starch, the method of making such starch, and uses thereof.

BACKGROUND OF THE INVENTION

This invention relates to a highly resistant granular starch with high dietary fiber content which may be prepared by the selected heat-moisture treatment of high amylose starch and then treating the starch with amylase to obtain a highly resistant starch. Further, the invention relates to the use of this highly resistant granular starch in food products.

Starch, a complex carbohydrate, is composed of two types of polysaccharide molecules, amylose, a mostly linear and flexible polymer of D-anhydroglucose units that are linked by alpha-1,4-D-glucosidic bonds, and amylopectin, a branched polymer of linear chains that are linked by alpha-1,6-D-glucosidic bonds. Starch is digested predominantly in the small intestine by the enzyme alpha-amylase. Alpha-amylase hydrolyzes alpha-1,4-D-glucosidic bonds, but does not hydrolyze the alpha-1,6-D-glucosidic linkages, resulting in less complete hydrolysis of the amylopectin fraction.

It is known that certain starch processing operations result in the transformation of starch into starch that is resistant to pancreatic amylase, known simply as resistant starch. Resistant starch resists digestion by pancreatic alpha-amylase and absorption in the small intestine, but passes into the large intestine where it is fermented by colonic microflora to short chain fatty acids and gases. Research literature indicates that this fermentation of resistant starch by colonic bacteria has numerous beneficial effects including colonic health and reduces the chances of developing diverticulosis and colon cancer. Further, as it is not utilized until it reaches the large intestine, where it is fermented to short chain fatty acids, resistant starch has a reduced caloric value and in respect of these properties has the benefits of dietary fiber.

Resistant starch (RS) has been classified in the literature into four categories depending on the causes of resistance. RS1 is a physically inaccessible starch due to entrapment of granules within a protein matrix or within a plant cell wall. RS2 is a granular starch that resists digestion by pancreatic alpha-amylase. RS3 is a retrograded, nongranular starch formed by heat/moisture treatment of starch or starch foods. RS4 is a chemically modified starch that resists digestion by alpha-amylase and includes acetylated, hydroxy propylated, or cross-linked starches.

Various methods have been reported for producing the various types of resistant starch. These include U.S. Pat. No. 5,593,503 which describes a method of making a resistant starch of the RS2-type; U.S. Pat. Nos. 5,281,276 and 5,409,542 which describe methods of making resistant starches of the RS3-type; and U.S. Pat. No. 5,855,946 which describes a method of making a resistant starch of the RS4-type.

However, unless highly crosslinked, these resistant starches are not highly resistant and commercially resistant starches typically have a resistance in the range of about 35–65%. Due to the benefits of resistant starch, more highly resistant starches which are chemically unmodified would be important and of great value.

More highly resistant starches are known and are described for example in U.S. Pat. No. 5,051,271 and WO 90/15147. However, these highly resistant starches are non-granular.

Surprisingly, it has now been discovered that highly resistant granular starch can be prepared and that such starch has unique and useful properties.

SUMMARY OF THE INVENTION

Highly resistant granular starches may be produced which have unique and useful properties, including high resistance, high dietary fiber, a unique molecular weight distribution, a high melting temperature and a high heat of gelatinization (Delta H) indicative of excellent processing tolerance. These starches may be prepared for example by heating a high amylose starch having at least 40% amylose content by weight at a percent moisture and temperature insufficient to destroy the granular nature of the starch, and digesting the amorphous regions, e.g. by using alpha-amylase or a chemical reagent This invention further relates to food products which contain the highly resistant granular starch with high dietary fiber content, particularly those prepared using the heat-moisture treatment as described herein.

DETAILED DESCRIPTION OF THE INVENTION

Figure 1:
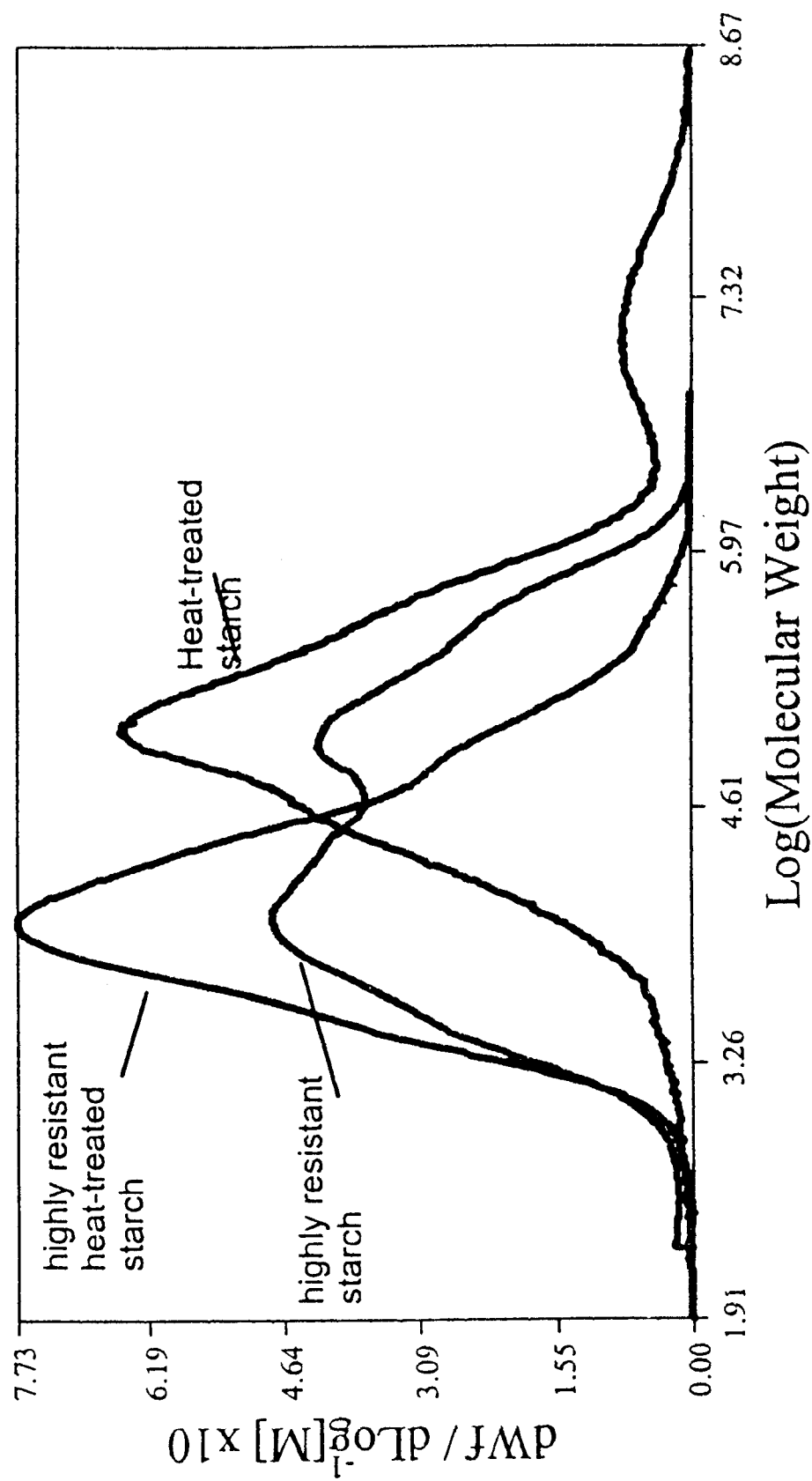
FIG. 1 depicts the molecular weight distributions of a highly resistant granular starch, a resistant heat-treated granular starch, and a highly resistant heat treated granular starch of the present invention all prepared from a high amylose base starch.

The term "resistant starch (RS)" as used herein is defined as the sum of starch and starch degradation products that are not absorbed in the small intestine of healthy individuals and may be measured by a variety of tests known in the art. As used herein, resistant starch is defined as measured by treatment with pancreatic alpha amylase in the test described, infra. The term "total dietary fiber content (TDF)" as used herein is defined as measured by the Prosky et al. method, Journal of Association of Official Analytical Chemists (AOAC), 68: 677 (1985).

The starches used in preparing alpha-amylase resistant granular starch may be any native amylose-containing starch derived from any native source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch or derived from a plant grown from induced mutations and variations of the above generic composition which may be produced by known standard methods of mutation breeding are also suitable herein.

Typical sources for the starches are cereals, tubers, roots, legumes and fruits. The native source can be corn, pea, potato, sweet potato, banana, barley, wheat, rice, sago, amaranth, tapioca, arrowroot, canna, sorghum, and high amylose varieties thereof. As used herein, the term "high amylose" is intended to include a starch containing at least about 40% amylose by weight. High amylose starch has been found to be most suitable for use in this invention.

It is well known that starch is composed of two fractions, the molecular arrangement of one being linear and the other being highly branched. The linear fraction of starch is known as amylose and the branched fraction amylopectin. Starches from different sources are characterized by different relative proportions of the amylose and amylopectin components. Some plant species have been genetically developed which are characterized by a large preponderance of one fraction over the other. For instance, certain varieties of corn which normally contain about 22 to 28% amylose have been developed which yield starch composed of over 40% amylose. These hybrid varieties have been referred to as high amylose.

High amylose corn hybrids were developed in order to naturally provide starches of high amylose content and have been available commercially since about 1963. Suitable high amylose starches useful herein are any starches with an amylose content of at least 40%, particularly at least 65% by weight.

The starch material useful in this invention also may include high amylose flour where the starch component of the flour contains at least 40% by weight of amylose. The term starch as used throughout this application is intended to include flour and when the high amylose content of flour is referred to throughout the application and claims, it is understood to refer to the amylose content of the starch component of the flour (e.g., 40% by weight of amylose based on the amount of starch in the flour). Such flour typically comprises protein (about 8 to 13% by weight), lipids (up to about 3% by weight) and starches (about 80 to 90% by weight) which include the specified high amylose content.

Another useful high amylose starch is a substantially pure starch extracted from a plant source having an amylose extender genotype, the starch comprising less than 10% by weight amylopectin. This starch which is useful as the starch base material is derived from a plant breeding population, particularly corn, which is a genetic composite of germplasm selections and comprises at least 75% by weight amylose, optionally at least 85% amylose (i.e., normal amylose) as measured by butanol fractionation/exclusion chromatography techniques. The starch further comprises less than 10%, by weight, optionally less than 5%, amylopectin and additionally from about 8 to 25% low molecular weight amylose. The starch is preferably extracted in substantially pure form from the grain of a starch bearing plant having a recessive amylose extender genotype coupled with numerous amylose extender modifier genes. This starch and the method of preparation are described in U.S. Pat. No. 5,300,145 which is incorporated herein by reference.

In preparing the resistant granular starch of this invention it is necessary that the base starch have a specified amount of water or moisture content and is heated to a defined temperature. By treating the starch under these conditions, a granular resistant starch having a high amount of total dietary fiber content, as described hereinafter, will be prepared.

The starch will be heated at a moisture content and temperature insufficient to destroy the granular nature of the starch. The total moisture or water content of the starch to be heat treated will typically be in a range of from about 10 to 80% by weight, particularly 20 to 45 and more particularly from about 30 to 40% by weight, based on the weight of the dry starch. In particular, this relative level of moisture is maintained during a substantial portion of the heating step.

The starch with specified moisture content is typically heated at a temperature of from about 60 to 160° C., particularly from about 90 to 120° C. While the most desirable temperature may vary depending on the particular starch and its amylose content as well as the moisture of the starch, it is important the starch remain in the granular state and not lose its birefringent characteristic. Also, the time of heating can vary depending on the starch used, its amylose content, the level of total dietary fiber content desired as well as the amount of moisture and the heating temperature. Typically the heating time will be from about 0.5 to 24 hours, particularly from about 1 to 4 hours.

The most desired conditions for treating starch to obtain a high level of total dietary fiber are such that the granular structure of the starch is not destroyed and the granules are still birefringent. Further, there would be evident a maltese cross when the granular structure is viewed under polarized light. However, there may be some conditions, such as at high moisture and high temperature, where the starch granule may be partially swollen but the crystallinity is not completely destroyed. Under these conditions, the starch granule has not been completely destroyed and an increase in total dietary fiber may still be obtained in accordance with this invention. Accordingly, the term "granular starch" as used herein, means a starch which predominantly retains its granular structure and has some crystallinity, such that the granules are birefringent and the maltese cross is evident under polarized light.

Alternatively, the non-native, granular resistant starch may be prepared by other methods known in the art, for example according to the method described in U.S. Pat. No. 5,849,090.

After the granular resistant starch is produced, the remaining amorphous regions are removed. This can be accomplished, inter alia, by degradation using alpha-amylase and/or by treatment with at least one chemical reagent. Such chemical reagents are intended to include, without limit, organic and inorganic acids and their derivatives, including hydrochloric and sulfuric acid.

The enzymatic hydrolysis of the heat treated starch is carried out using techniques known in the art. The amount of enzyme used is dependent upon the enzyme, i.e., source and activity, and base material used as well as the amount of hydrolysis desired. Typically, the enzyme is used in an amount of from about 0.01 to about 2.0%, particularly from about 0.5 to 1.5%, by weight of the starch.

The optimum parameters for enzyme activity will vary depending upon the enzyme used. The rate of enzyme degradation depends upon factors known in the art, including the enzyme used, enzyme concentration, substrate concentration, pH, temperature, the presence or absence of inhibitors, and the degree and type of any modification. These parameters may be adjusted to optimize the digestion rate of the starch base.

Generally the enzyme treatment is carried out in an aqueous or buffered slurry at a starch solids level of about 5 to about 40%, depending upon the base starch being treated. A solids level of from about 15 to 35% is particularly useful, from about 18 to 25% more particularly useful, in the instant invention. Typically, enzyme digestion is carried out at the highest solids content feasible without reducing reaction rates in order to facilitate any desired subsequent drying of the starch composition. In the alternative, the process may utilize an enzyme immobilized on a solid support.

The enzyme treatment may also be carried out using high solids. In this process which is described in EP 806 434, the starch, water (usually in an amount of no more than 35% by weight based upon the weight of the starch), and enzyme are mixed in an amount sufficient to produce a single phase powdered mixture without a visible free water phase and the enzyme is heat activated. The pH and temperature of the reaction should be adjusted to provide effective enzyme hydrolysis. These parameters are dependent upon the enzyme to be used and are known in the art. In general, a temperature of about 22 to about 65° C. is used, particularly from about 30 to about 45° C. In general, the pH is adjusted to about 3.5 to about 7.5, particularly from about 4.5 to about 7.0, using techniques known in the art.

The enzyme reaction is continued until the desired level of resistance has been achieved. Generally, a significant portion of the amorphous regions of the starch is digested to achieve a high resistance, particularly a resistance of at least about 70%, more particularly a resistance of at least about 80%, by weight of the starch.

In general, the enzyme reaction will take from about 0.1 to about 24 hours, particularly about 0.5 to about 6 hours. The time of the reaction is dependent upon the type of starch and enzyme used, the amount of enzyme used, and the reaction parameters of solids percent, pH, and temperature.

The enzyme degradation may then be terminated by any technique known in the art such as acid or base deactivation. For example, acid deactivation may be accomplished by adjusting the pH to lower than 2.0 for at least 30 minutes. Heat deactivation is typically not suitable if a granular product is desired as the heat necessary to deactivate the enzyme will generally also gelatinize the starch.

Alternatively, hydrolysis of the starch may be accomplished by the action of a chemical reagent, particularly hydrochloric or sulfuric acid. Acid hydrolysis is typically done by adding an acid to an aqueous starch slurry under agitation at a temperature ranging from ambient to a few degrees below the starch gelatinization temperature and stirring until the desired level of resistance is achieved. The acid is then neutralized with a typical neutralizing base, such as $NaHCO_3$ or NaOH. Methods and conditions of acid hydrolysis are well known in the art and may be found in O.P. Wurzburg, Modified Starches: Properties and Uses, CRC Press Inc., (1986) Baca Raton, Fla. pp. 17–24.

After the hydrolysis, either enzymatic or by chemical reagent, the starch is filtered to remove the solubles, optionally washed, and may be allowed to air dry to reach equilibrium moisture conditions or may be dried using a flash dryer or other drying means.

The starch may be modified by treatment with any reagent or combination of reagents provided the modification does not destroy the granular nature of the starch. Chemical modifications may be conducted on the base starch, before or after heat treatment and/or before or after hydrolysis. Chemical modifications are intended to include crosslinked starches, acetylated and organically esterified starches, hydroxyethylated and hydroxypropylated starches, phosphorylated and inorganically esterified starches, cationic, anionic, nonionic, and zwitterionic starches, and succinate and substituted succinate derivatives of starch. Such modifications are known in the art, for example in Modified Starches: Properties and Uses, Ed. Wurzburg, CRC Press, Inc., Florida (1986). Other suitable modifications and methods are disclosed in U.S. Pat. Nos. 4,626,288, 2,613,206 and 2,661,349, which are incorporated herein by reference.

The resulting chemically modified or unmodified starch product which has been heat treated and hydrolyzed will still have a granular structure as evidenced by its birefringent characteristic when viewed under the microscope and by a maltese cross when viewed under polarized light. The granular resistant starch product will have a total dietary content of at least about 20%, particularly at least about 40%, more particularly at least about 50% by weight. The granular resistant starch product will have a resistant starch content of at least about 70% and particularly at least about 80% by weight of the starch. The levels of dietary fiber resistant starch will vary depending on the conditions used as well as the particular starch starting material.

The resulting starch product is also characterized by a molecular weight peak at from about 2,000 to 80,000, particularly about 5,000 to 20,000 daltons.

The resulting granular starch product is further characterized by a high onset, peak and end melting temperature as well as a high heat of gelatinization (Delta H) as shown by differential scanning colorimetry (DSC) compared to highly resistant native granular starch. In particular the resulting starches have an onset melting temperature of at least about 90° C., particularly at least about 95° C., and a peak temperature of at least about 110° C., particularly at least about 120° C. Further, the resulting starches have a Delta H of at least about 20 J/g. The high melting temperature and Delta H are indicative of high process tolerance. Thus, the resulting starches will at least maintain and possibly even increase their resistance and total dietary fiber during processing under typical processing temperatures and shear.

The granular resistant starch product of this invention may be used in any food or beverage product (hereinafter collectively referred to as foods) to contribute to the total dietary fiber and resistant starch present as well as to reduce the caloric content. Typical food products include, but are not limited to, cereals such as ready-to-eat, puffed or expanded cereals and cereals which are cooked before eating; baked goods such as breads, crackers, cookies, cakes, muffins, rolls, pastries and other grain-based ingredients; pasta; beverages; fried and coated foods; snacks; and cultured dairy products such as yogurts, cheeses, and sour creams.

The amount of granular resistant starch and dietary fiber which can be added and used in any given food will be determined to a great extent by the amount that can be tolerated from a functional standpoint. In other words, the amount of granular resistant starch and fiber used generally will be as high as will be acceptable in organoleptic evaluation of the food. Generally the granular resistant starch may be used in food applications at about 0.1 to 50%, by weight of the food and more particularly from about 1 to 25% by weight.

The granular resistant starch of this invention may also be used in a pharmaceutical or nutritional product, including but not limited to prebiotic and synbiotic compositions, diabetic foods and supplements, dietetic foods, foods to control glycemic response, and tablets and other pharmaceutical dosage forms. A prebiotic composition is a nondigestible food ingredient that beneficially affects the host by selectively stimulating the growth, activity or both of one or a limited number of bacterial species already resident in the colon. A synbiotic composition may be a yogurt, capsule or other form of introduction into the host animal, including human beings, in which prebiotics are used in combination with a live microbial food supplement. The live microbial food supplement beneficially affects the host animal by improving its intestinal microbial balance.

Such live microbial food supplements may include, without limit, yeasts such as Saccharoymyces, and bacteria such as the genera Bifobacterium, Bacteriodes, Clostridium, Fusobacterium, Propionibacterium, Streptococcus, Enterococcus, Lactococcus, Staphylococcus, Peptostreptococcus and Lactobacillus.

EXAMPLES

The following examples are presented to further illustrate and explain the present invention and should not be taken as limiting in any regard. All parts and percentages are given by weight and all temperatures in degrees Celsius (° C.) unless otherwise noted.

The following ingredients were used throughout the examples.

HYLON® VII starch commercially available from National Starch and Chemical Company.

Pancreatin, product #P-7545, commercially available from Sigma Chemical company.

The following test procedures were used throughout the examples.

A. Resistant Starch Determination

The amount of resistant starch is determined as follows:
SAMPLE PREPARATION
(1) Put 2.0 g (dry weight) of test starch in jar.
(2) Add 0.05 M phosphate buffer with 4% NaCl to bring total weight to 42.0 g.
(3) Place magnetic stir bar in jar, mix well, and cap tightly.
(4) Equilibrate in a 37° C. shaker bath for 5 min.
BLANK DETERMINATION
(1) Carefully pipet 1.0–1.5 mL of each sample into microcentrifuge tubes. Replace excess sample contained in pipet in the appropriate jar.
(2) Centrifuge at 10,000 rpm for 2 min.
(3) Measure solubles of one drop of supernatant by refractometer, which has been zeroed with DI water.
(4) Replace remaining sample from centrifuge tube back into jar.
ENZYME ADDITION
(1) Add 8 mL of 5% pancreatin. Start timer.
(2) Mix well, cap tightly, and incubate in shaker bath at 37° C.
SAMPLING PROCEDURE (after 6 hours)
(1) Pipet 1.5 mL of sample into microcentrifuge tube.
(2) Centrifuge at 10,000 rpm for 2 min.
(3) Measure solubles of supernatant by refractometer, which has been zeroed with DI water. From the percent solubles, the amount of starch digested may be calculated. Resistant starch is the amount of starch not digested.

B. Total Dietary Fiber Determination

The following procedure outlines the determination of total dietary fiber ("TDF") content using the Megazyme TDF Test Kit (commercially available from Megazyme Int. Ireland, Ltd.) which is based upon the AOAC method 985.29.
TDF ASSAY KIT:
Kits with reagents of 200 assays are available from Megazyme and contain:
1. Full assay method.
2. Thermostable α-amylase (20 mL) (Megazyme E-BLAAM).
3. Purified protease (20 mL) (Megazyme E-BSPRT).
4. Purified amyloglucosidase (2×20 mL) (150% the concentration in other TDF kits) (Megazyme E-AMGDF).
Celite®545 (hereinafter "Celite"), acid washed in 100 g or 500 g packages is available separately (G-CEL100; or G-CEL500)
APPARATUS:
Dispensers
a. 280±2.0 mL for 95% ethanol.
b. 10±0.5 mL for 78% EtOH, 95% ethanol, and acetone.
c. 50±0.5 mL for buffer.

REAGENTS:
1. Phosphate buffer, 0.08 M, pH 6.0. Dissolve 1,400 g Na phosphate anhydrate ($Na_2HPO_4$) (or 1.753 g dihydrate) and 9.68 g Na phosphate monobasic monohydrate ($NaH_2PO_4$) (or 10.94 g dihydrate) in approximately 700 mL distilled water. Dilute to 1 L with water. Check pH with pH meter.
2. Sodium hydroxide solution, 0.275 N. Dissolve 11.00 g ACS grade NaOH in approximately 700 mL disstilled water, using appropriate handling precautions, in 1 L volumetric flask. Cool and dilute to volume with water.
3. Hydrochloric acid solution, 0.325 N. Dilute stock solution of known titer (i.e. 325 mL of 1.0 N HCl) to 1 L with water in volumetric flask.
PROCEDURE:
Preparation of Sample
Total dietary fibre should be determined on an as-is basis on dried, low-fat or fat-free sample. Homogenize sample and dry overnight in 70° C. vacuum oven. Cool in desiccator, reweigh, and record weight loss due to drying. Dry-mill portion of dried sample to 0.3–0.5 mm mesh. If sample cannot be heated, freeze-dry before milling. If high fat content (<10%) previous proper milling, defat with petroleum ether three times with 25 mL portions (per g of sample) before milling. When analyzing mixed diets, always extract fat before determining total dietary fibre.

Record weight loss due to fat. Correct final % dietary fibre determination for both moisture and fat removed. Store dry-milled sample in capped jar in desiccator until analysis is run.
METHOD
Run blank through entire procedure along with samples to measure any contribution from reagents to residue.
1. Weigh duplicate 1 g samples, accurate to 0.1 mg, into 400 mL tall-form beakers. Sample weights should differ by less than 20 mg from each other. Add 50 mL phosphate buffer (pH 6.0) to each beaker and check pH with pH meter. Adjust if pH does not equal 6.0±0.1.
2. Add 50 μL heat-stable α-amylase solution.
3. Cover beaker with aluminum foil and place in boiling water bath for 15 minutes. Shake gently at 5 minute intervals. Note: Increase incubation time when number of beakers in bath makes it difficult for beaker contents to reach internal temperature of 100° C. Use thermometer to indicate that 15 min at 100° C. Use thermometer to indicate that 15 min at 100° C. is attained. Total of 30 min in boiling water bath should be sufficient.
4. Cool solutions to room temperature.
5. Adjust to pH 7.5±0.1 by adding 10 mL 0.275 N NaOH solution. Check pH with pH meter.
6. Add 100 μL of protease solution.
7. Cover beaker with aluminum foil and incubate at 60° C. with continuous agitation for 30 min.
8. Cool and add 10 mL 0.325 N HCl solution to adjust pH to 4.5±0.2. Check pH with pH meter.
9. Add 200 μL amyloglucosidase, cover with aluminum foil, and incubate 20 min at 60° C. with continuous agitation.
10. Add 280 mL 95% ethanol ("EtOH") preheated to 60° C. (measure volume before heating). Let precipitate form at room temperature for 60 min.
11. Weigh crucible containing Celite to nearest 0.1 mg, then wet and distribute bed of in crucible by using stream of 78% EtOH from wash bottle.
12. Apply suction to draw Celite onto fritted glass as even mat. Maintain suction and quantitatively transfer precipitate from enzyme digest to crucible.
13. Wash residue successively with three 20 mL portions of 78% EtOH, two 10 mL portions of 95% EtOH, and two 10 mL portions of acetone. In some cases, gums may form during filtration, trapping liquid in residue. If so, break surface film with spatula to improve filtration. Long filtration times can be avoided by careful intermittent suction throughout filtration.
14. Dry crucible containing residue overnight in 70° C. vacuum oven or 105° C. air oven.
15. Cool in desiccator and weigh to nearest 0.1 mg. Subtract crucible and Celite weights to determine weight of residue.
16. Analyze residue from one sample of set of duplicates for protein by AACC Method 46–13, using N×6.25 as conversion factor.
17. Incinerate second residue sample of duplicate for 5 hr at 525° C. Cool in desiccator and weigh to 0.1 mg. Subtract crucible and Celite weights to determine ash.

CALCULATIONS

Uncorrected average blank residue (UBAR) Average blank residue of duplicate Blanks (from step 15) in mg
Blank protein residue (BPR)=UABR×% protein in blank (step 16)/100
Blank ash residue (BAR)=UABR×% ash in blank (step 17)/100
Corrected blank (CB)=UABR−BPR−BAR
Uncorrected average sample residue (USAR)=Average sample residue of duplicate samples (from step 15) in mg
Sample protein residue (SPR)=USAR×% protein in sample (step 16)/100
Sample ash residue (SAR)=USAR×% ash in sample (step 17)/100
Corrected sample residue (CSR)=USAR−SPR−SAR−CB
% TDF=100×CSR/mg sample

C. Differential Scanning Calorimetry ("DSC") Measurements

Differential scanning calorimetry measurements were performed in a Perkin-Elemr DSC-7 (Norwalk, Coon., U.S.A.). The instrument was calibrated with indium. Samples (approximately 10 mg of starch) at a starch-to-water ratio of 1:3 were prepared and heated at 10° C./minute from 5° C. to 160° C. An empty stainless-steel pan was used as a reference.

Example 1

Preparation of a Highly Resistant Heat-Treated Granular Starch a. A sample of HYLON® VII starch (moisture=10.6%) was mixed with sufficient water to at room temperature to obtain a total water content of 38%. The temperature was raised to about 210° F. and the sample was held at this temperature for two hours while maintaining the moisture content of the system. The resultant heat-treated starch was dried to about 12% moisture and cooled.
200 g of the heat-treated starch sample was diluted with 4400 ml of 0.05 NaH$_2$PO$_4$ containing 4% NaCl. The pH was adjusted to 6.9 and the temperature was adjusted to 37° C. 0.8% pancreatin (w/w based on starch sample) was added. After 8 hours, the enzyme was deactivated. The samples were filtered, washed, dried, and ground to pass through a 40 mesh sieve.
b. Example 1a was repeated using a low amylopectin starch prepared in accordance with U.S. Pat. No. 5,300,145 except that the moisture content during heat treatment was 20% and heat treatment was conducted at 260° F. for three hours.

Example 2

Preparation of a Highly Resistant Native Granular Starch a. A 200 g sample of HYLON® VII starch (moisture=10.6%) was diluted with 4400 ml of 0.05 NaH$_2$PO$_4$ containing 4% NaCl. The pH was adjusted to 6.9 and the temperature was adjusted to 37° C. 0.8% pancreatin (w/w based on starch sample) was added. After 8 hours, the enzyme was deactivated. The samples were filtered, washed, dried, and ground to pass through a 40 mesh sieve.
b. Example 2a was repeated using a low amylopectin starch prepared in accordance with U.S. Pat. No. 5,300,145.

Example 3

Preparation of a Heat Treated Granular Starch a. A sample of HYLON® VII starch (moisture=10.6%) was mixed with sufficient water to at room temperature to obtain a total water content of 38%. The temperature was raised to about 210° F. and the sample was held at this temperature for two hours while maintaining the moisture content of the system. The resultant heat-treated starch was dried to about 12% moisture and cooled.
b. Example 3a was repeated using a low amylopectin starch prepared in accordance with U.S. Pat. No. 5,300,145 except that the moisture content during heat treatment was 20% and heat treatment was conducted at 260° F. for three hours.

Example 4

Comparison of Resistant Starches

The total dietary fiber content, resistant starch content, onset, peak and end melting temperature, and heat of gelatinization of the resistant starches of Examples 1a, 2a, and 3a were determined. The results are shown in the table, below.

| Sample | TDF % | RS % | $T_{onset}$ (° C.) | $T_{peak}$ (° C.) | $T_{end}$ (° C.) | ΔH (J/g) |
|---|---|---|---|---|---|---|
| Example 1a | 50 | 90 | 99.6 | 121.5 | 158.5 | 33.1 |
| Example 2a | 14 | 80 | 74.4 | 96.4 | 126.2 | 17.2 |
| Example 3a | 62 | 54 | 94.7 | 107.3 | 132.5 | 19.8 |

The data reported in the Table above indicates that enzyme digestion of a highly pure, heat-treated starch produces a highly resistant starch (Example 1a) with desirable properties. For instance, Example 1a had advantageously higher onset temperatures than either the undigested heated treated starch (Example 3a) or a highly pure resistant starch made from native starch (Example 2a).

We claim:
1. A resistant starch characterized by:
   a) a granular structure;
   b) a molecular weight peak at from about 2,000 to about 80,000 daltons;
   c) an onset melting temperature of at least about 90° C.;
   d) a peak melting temperature of at least about 110° C.;
   e) a heat of gelatinization of at least about 20 J/g; and
   f) a resistant starch content of at least about 70% by weight.

2. The resistant starch of claim 1, wherein the molecular weight peak is from about 5,000 to about 20,000 daltons.

3. The resistant starch of claim 1, wherein the onset melting temperature is at least about 95° C.

4. The resistant starch of claim 1, wherein the peak melting temperature is at least about 120° C.

5. The resistant starch of claim 1, wherein the starch has a resistant starch content of at least about 80% by weight.

6. A food product containing the resistant granular starch of claim 1 and having a total dietary fiber content of at least 20%.

7. The food product of claim 6 selected from the group consisting of cereal, bread, crackers, cookies, cakes, pasta, beverages, fried and coated foods, snacks, and cultured dairy products.

8. The resistant starch of claim 1 wherein the molecular weight peak is from about 5,000 to about 20,000 daltons, the onset melting temperature is at least about 95° C., the peak melting temperature is at least about 120° C., and the starch has a resistant starch content of at least about 80% by weight.

9. A method for preparing a resistant granular starch with increased total dietary fiber content comprising:
   a) heating a high amylose starch having at least 40% by weight amylose content under a combination of moisture and temperature conditions such that the starch remains in the granular state and is birefringent, the total moisture content of the starch being from about 10 to 80% by weight and the temperature being from about 60° C. to 160° C., and
   b) removing the amorphous regions; the resultant resistant granular starch characterized by a total dietary fiber content of at least about 20% and a resistant starch content of at least about 80%.

10. The method of claim 9, wherein removing the amorphous regions is accomplished by the method comprising treatment with alpha-amylase.

11. A food product containing a resistant granular starch prepared by the method of claim 10 and having a total dietary fiber content of at least 20%.

12. The method of claim 9, wherein removing the amorphous regions is accomplished by the method comprising treatment with at least one chemical reagent.

13. The method of claim 9 wherein the high amylose starch has a total moisture content of from about 20 to 45% and the starch is heated at a temperature of from about 90° C. to 120° C.

14. The method of claim 9 wherein the high amylose starch is a high amylose corn starch.

15. The method of claim 9 wherein the high amylose starch is chemically modified.

16. The method of claim 9 wherein the high amylose starch has a total moisture content of from about 30 to 40% by weight and the heating is at a temperature of from about 90° C. to 120° C.

17. The method of claim 9 wherein the high amylose starch has at least 65% by weight amylose content.

18. The method of claim 17, wherein the high amylose starch has a total moisture content of from about 20 to 45% and the heating is at a temperature of from about 90° C. to 120° C.

19. The method of claim 18 wherein the granular starch product has a total dietary fiber content of at least 40%.

20. The method of claim 9 wherein the high amylose starch is a substantially pure starch extracted from a plant source having an amylose extender genotype the starch comprising less than 10% amylopectin determined by butanol fractionation/exclusion chromatography measurement.

21. The method of claim 20 wherein the high amylose starch has a total moisture content of from about 20 to 45% and the heating is at a temperature of from about 90° C. to 120° C.

22. A food product containing a resistant granular starch prepared by the method of claim 9 and having a total dietary fiber content of at least 20%.

* * * * *